United States Patent
Echeverri-Lopez et al.

(10) Patent No.: US 9,168,268 B1
(45) Date of Patent: Oct. 27, 2015

(54) **SAPONINS AND CHROMANS DERIVATIVES MIXTURE COMPOSITIONS AGAINST LEISHMANIASIS, TRYPANOSOMIASIS AMERICANA, MALARIA, TRYPANOSOMIASIS AFRICANA AND *FASCIOLA HEPATICA***

(71) Applicant: UNIVERSIDAD DE ANTIOQUIA, Medellin (CO)

(72) Inventors: Luis Fernando Echeverri-Lopez, Medellin (CO); Winston Quinones-Fletcher, Medellin (CO); Luis Fernando Torres-Roldan, Medellin (CO); Rosendo Ricardo Archbold-Joseph, Medellin (CO); Gustavo Adolfo Escobar-Pelaez, Medellin (CO); Sara Maria Robledo-Restrepo, Medellin (CO); Ivan Dario Velez-Bernal, Medellin (CO); Diana Lorena Munoz-Herrera, Medellin (CO); Adriana Maria Restrepo-Agudelo, Medellin (CO); Juan Alejandro Daza-Figueredo, Medellin (CO); Sergio Andres Pulido-Munoz, Medellin (CO); Edwin Andres Correa-Garces, Medellin (CO)

(73) Assignee: Universidad de Antioquia, Medellin (CO)

( * ) Notice: Subject to any disclaimer, the term of this patent is extended or adjusted under 35 U.S.C. 154(b) by 203 days.

(21) Appl. No.: 13/859,717

(22) Filed: Apr. 9, 2013

(51) Int. Cl.
*A61K 31/704* (2006.01)
*A61K 31/382* (2006.01)
*A61K 31/353* (2006.01)

(52) U.S. Cl.
CPC .............. *A61K 31/704* (2013.01); *A61K 31/353* (2013.01); *A61K 31/382* (2013.01)

(58) Field of Classification Search
USPC ........ 514/33; 536/4.1, 18.1, 18.2; 549/13, 57, 549/60, 64; 546/1, 152, 156
See application file for complete search history.

(56) References Cited

PUBLICATIONS

Munoz, D. L. et al, Vitae, 2006, 13(2), 5-12, English Translation.*

* cited by examiner

*Primary Examiner* — Ganapathy Krishnan
(74) *Attorney, Agent, or Firm* — Hoglund & Pamias, PSC; Roberto J. Rios

(57) ABSTRACT

SAPONINS AND CHROMANS DERIVATIVES MIXTURE COMPOSITIONS AGAINST LEISHMANIASIS, TRYPANOSOMIASIS AMERICANA, MALARIA, TRYPANOSOMIASIS AFRICANA AND *FASCIOLA HEPATICA*, is a composition of saponins and chromans derivatives. The saponins are triterpene types and chromans are hydrazones derivatives. This composition is a therapeutic agent against tropical diseases.

12 Claims, 3 Drawing Sheets

SAPONINS AND CHROMANS DERIVATIVES MIXTURE COMPOSITIONS AGAINST LEISHMANIASIS, TRYPANOSOMIASIS AMERICANA, MALARIA, TRYPANOSOMIASIS AFRICANA AND FASCIOLA HEPATICA

BACKGROUND OF THE INVENTION

This invention belongs to the field of chemistry and relates to a formulation of saponins and chromans derivatives mixtures. The saponins are triterpenes types and chromans (TC) are hydrazones derivatives. This formulation is a therapeutic agent against tropical diseases for parenteral use and/or topical use.

Tropical medicine is the branch of medicine that deals with health problems that occur uniquely, are more widespread, or prove more difficult to control in tropical and subtropical regions. In practice, the term is often taken to refer to infectious diseases that thrive in hot, humid conditions, such as leishmaniasis, malaria, schistosomiasis, onchocerciasis, lymphatic filariasis, Chagas disease, African trypanosomiasis, and dengue.

Tropical diseases blight the lives of a billion people worldwide and threaten the health of millions more. An evaluation of their significance to public health and economies has convinced governments, donors, the pharmaceutical industry and other agencies, including nongovernmental organizations, to invest in preventing and controlling this diverse group of diseases.

Parasitic diseases caused by protozoan parasites such as *Leishmania* spp and *Trypanosoma cruzi* are affecting thousands of people around the world. Leishmaniasis is prevalent disease in 88 countries worldwide affecting 12 million people with 2.000.000 new cases per year, accounting for 500.000 cases of visceral leishmaniasis and 1.500.000 of cutaneous leishmaniasis. On the other hand, about 7.5 million people are infected with *T. cruzi* in 21 Latin-American countries, with approximately 41.000 new cases per year.

The massive displacement of populations, weather change, growing resistance to drugs treatment, lack of therapeutic alternatives and long treatments are creating a significant rise in these diseases, with the resulting increase in public health problems, mainly regarding poor people.

Solutions exist against the leishmaniasis like patents U.S. Pat. No. 8,287,921, EP 2337560, EP 2241317 A1, U.S. Pat. No. 6,872,713 and publication number US 2012/0207821 A1.

EP 2241317 A1 "Domperidone at a low daily dose for use in the treatment or prevention of a disease associated with an alteration of the immune response" (Ochoa, P., Homedes, J., Sabate, D.) 31 Mar. 2009 that relates to the use of domperidone or a pharmaceutically acceptable salt thereof at low doses to prevent and/or treat a disease associated with an alteration of the immune response such as Leishmaniasis.

Publication number US 2012/0207821 A1 "Liposomal formulation and use thereof" (Ali, N., Ghose, J., Bhowmick, S.) 10 May 2010 presents a liposomal formulation useful as a leishmanicidal agent, wherein said formulation comprising a single dose of therapeutically effective amount of an antileishmanial antimonial drug encapsulated in a cationic liposome consisting of a neutral lipid and a cationic lipid in a molar ratio of 7:2 respectively, wherein molar ratio of the neutral lipid and the cationic lipid to said drug is 7:2:0.2 to 0.25.

The U.S. Pat. No. 8,287,921 "Formulations against cutaneous leishmaniasis" (Rahman, Choudhary, Yousuf, Khan, Soomro, Perveen) 24 Jul. 2011 consisting essentially of a therapeutically effective amount of an ethyl acetate extract of aerial parts of Physalis minima dispersed in petroleum.

EP 2337560 A1 (WO2010017613A1) "Use of 5-hydroxy-2-hydroxymethyl-y-pyrone (hmp) as a leishmanicidal agent" (ALVES, CARVALHO, NASCIMENTO, Drumond, Silva, Oliveira) 14 Ago 2009 refers to the use of HMP (a secondary metabolite obtained from *Aspergillus fungi*) as an agent that intensifies the mechanism of macrophage activation, leading to the death of L. (*Leishmania*) *amazonensis*, the etiologic agent of cutaneous leishmaniasis.

Also *Sapindus saponaria* resin contain saponins type hederagenin and has been employed in traditional medicine as antihelmintic, and these types of compounds are reported like leishmanicide too.

The U.S. Pat. No. 6,872,713 "Antiprotozoal saponins" (Louis Jules Roger Marie Maes, Nils Albert Gilbert Germonprez, Luc Emiel Mathilde Van Puyvelde, Norbert G. M. De Kimpe, Tran Ngoc Ninh) 29 Mar. 2005 refers to saponins of formula (I), a stereoisomeric form thereof or a pharmaceutically acceptable addition salt thereof, wherein R1 to R12 have the meaning given in the description, can be isolated from plants of the family Myrsinaceae and used, to decrease the infectiousness of and reduce the mortality associated with protozoan parasites of the genus *Leishmania* which are responsible for a group of conditions known as leishmaniases, but the new patent of this application in a formulation of saponins and chromans derivatives mixture with better therapeutic results.

With regard to the extract of *Sapindus saponaria*, the application of patent US 2011/0274777 A1 "Method for extraction of material from a Sapindacea family fruit" (Jaime Toro Restrepo, James Alberto Jimenez Martinez, Luis Fernando Echeverri Lopez, Sandra Patricia Zapata Porras) 10 May 2010 provides a standardized method to obtain a material from Sapindacea family fruits, wherein the material provides a preparation of material used in combination with *Swinglea glutinosa* extract for the preparation enhances the ability of the *Swinglea glutinosa* extract to kill and prevent fungi, and to kill and repel insects and mites. In the present application of patent a new formulation is obtained mixed an extract from *Sapindus saponaria* in quantities from 20% until 60% with synthetic chroman for use as therapeutic agent against tropical diseases like leishmaniasis, american trypanosomiasis, malaria, african trypanosomiasis and fasciolosis.

On the other hands, some saponins form *Maesa balansae* showed high activity in vitro and in vivo assays against *Leishmania*, but the instant invention is a formulation of saponins and chromans derivatives mixture, where the saponins are triterpene types and chromans are hydrazones derivatives.

SUMMARY OF THE INVENTION

The instant invention is a new formulation of saponins and chromans derivatives mixture compositions wherein the formulation is a therapeutic agent against tropical diseases like leishmaniasis, american trypanosomiasis, malaria, african trypanosomiasis and fasciolosis that contain synthetic chroman mixed with an specific extract of obtained from *Sapindus saponaria* for use parenteral and/or topical.

BRIEF DESCRIPTION OF THE DRAWINGS

These and other aspects and advantages of the present invention are more apparent from the following detailed description and claims, particularly when considered in conjunction with the accompanying drawings, in which:

DETAILED DESCRIPTION OF THE INVENTION

SAPONINS AND CHROMANS DERIVATIVES MIXTURE COMPOSITIONS AGAINST LEISHMANIASIS, TRYPANOSOMIASIS AMERICANA, MALARIA, TRYPANOSOMIASIS AFRICANA AND *FASCIOLA HEPATICA* is an invention related with the formulation of mixtures of several synthetic chroman derivative compounds with an extract of *Sapindus saponaria* resin containing triterpenoid saponins, to control human and animal diseases caused by parasite such as *Leishmania, Trypanosoma cruzi, Plasmodium, Trypanosoma brucei* and *Fasciola hepatica*. More specifically, the invention involved compounds of the Formula 1 related with synthetic chroman derivates compounds in a range from 10% until 80% of the formulation mixed with compounds of the Formula 2 related with extract of *Sapindus saponaria* resin mixed these with structures of the compound 1A, compound 2A and compound 3A in a range of the mixed extract from 20% until 90% of the formulation. The structures of the compound 1A, compound 2A and compound 3A are shown in FIG. 1.

Figure 1:
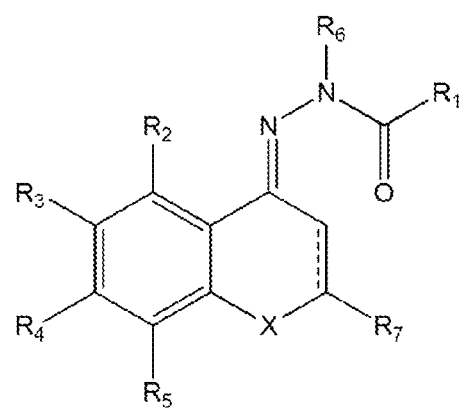
FIG. 1 shows the general structure of chroman derivatives, according to the present invention.
Figure 2:
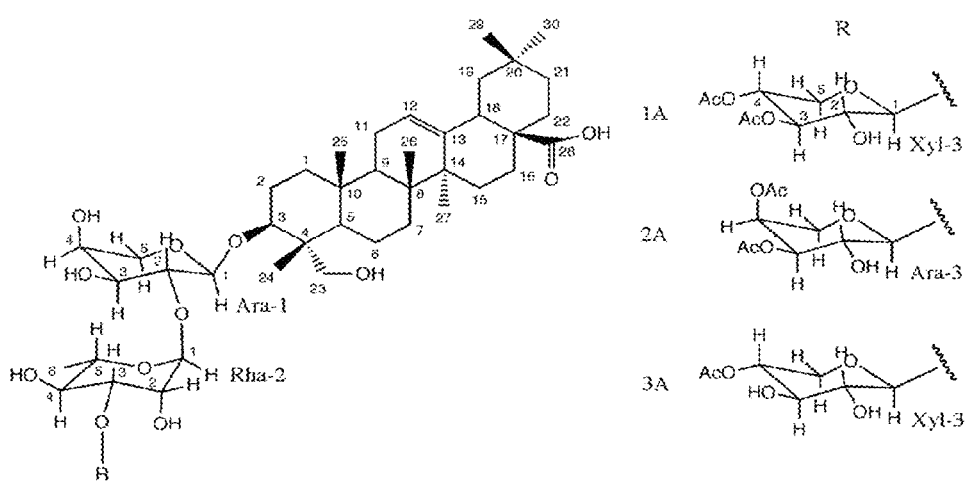
FIG. 2 shows the structure of compounds 1A $C_{48}H_{76}O_{17}$, 2A $C_{50}H_{78}O_{18}$, and 3A $C_{50}H_{78}O_{18}$, according to the present invention.

FIGS. 1 and 2 show the structure of synthetic chroman derivates compounds and compounds present in the extract of *Sapindus saponaria*, with structures of compound 1A, compound 2A and compound 3A. Specifically, FIG. 1 shows the general structure of chroman derivatives, wherein FIG. 2 shows the structure of compounds 1A $C_{48}H_{76}O_{17}$, 2A $C_{50}H_{78}O_{18}$, and 3A $C_{50}H_{78}O_{18}$.

The synthetic compounds in the Formula 1 are:

X represents O, NH, S (sulfone or sulfoxide isomers), or $CH_2$ and may or may not have a double bond in the position which establishes the figure as a dashed line.

$R_1$ represent phenyl, naphthyl, aromatic or not 5-6 membered hetero ring (containing 1-2 N atoms and 0-1 O atoms and 0-1 S atoms), mono o di substituted with substituent selects from the following group: H, OH, CHO, $OCH_3$, $NO_2$, $NH_2$, $NHCOCH_3$, COOH, $COOCH_3$, $CH_2OH$, CN, halogen, $C_1$-$C_6$ alkyl, $C_1$-$C_6$ alkylthio, $C_1$-$C_6$ haloalkyl, $C_1$-$C_6$ haloalkoxy or $C_1$-$C_6$ halothioalkyl.

$R_2$, $R_3$, $R_4$, $R_5$, $R_6$ and $R_7$ independently represent H, OH, CHO, $OCH_3$, $NO_2$, $NH_2$, $NHCOCH_3$, COOH, $COOCH_3$, $CH_2OH$, CN, halogen, $C_1$-$C_6$ alkyl, $C_1$-$C_6$ alkylthio, $C_1$-$C_6$ haloalkyl, $C_1$-$C_6$ haloalkoxy or $C_1$-$C_6$ halothioalkyl, —O—S (=O)—$R_8$, $N(R_9)SO_2R_{10}$, benzyl, phenyl. $R_8$=$C_1$-$C_6$ alkyl, $C_1$-$C_6$ alkylthio, $C_1$-$C_6$ haloalkyl, $C_1$-$C_6$ haloalkoxy or $C_1$-$C_6$ halothioalkyl.

$R_9$ and $R_{10}$ are $C_1$-$C_6$ alkyl, $C_1$-$C_6$ haloalkyl, $C_1$-$C_6$ haloalkoxy or $C_1$-$C_6$ halothioalkyl, un substituted or mono or di substituted phenyl or pyridil, with substituent selects from the following group: H, OH, CHO, $OCH_3$, $NO_2$, $NH_2$, $NHCOCH_3$, COOH, $COOCH_3$, $CH_2OH$, CN, halogen, $C_1$-$C_6$ alkyl, $C_1$-$C_6$ alkylthio, $C_1$-$C_6$ haloalkyl, $C_1$-$C_6$ haloalkoxy or $C_1$-$C_6$ halothioalkyl, all this compounds could be pure, isomer or tautomeric mixtures, for example syn/anti, cys/trans or R/S forms.

And the saponin mixtures shown in FIG. 2 are extracts obtained of triterpene saponins from *Sapindus saponaria* resin, wherein the extract contain not less than 80% of the mixture of saponins showed in the Formula 2, Rf=0.35, 0.45 and 0.60, detected by thin layer chromatography in silica gel plates, using dichloromethane-methanol (3:1) as eluent, and revealed with H2SO4 and heated. The synthetic chroman compounds of FIG. 1 are in proportions of 20 to 80% and the extract containing saponins of FIG. 2 in proportions of 20% to 80% is the best way to execute the invention, or mixtures of them. The formula shown in FIG. 1 related with synthetic chroman derivates compounds is mixed with compounds of the formula shown in FIG. 2 related with extract of *Sapindus saponaria* resin and mixed with structures of the compound 1A in range from 20% until 90% of the formulation, compound 2A in range from 20% until 90% of the formulation and compound 3A in range from 20% until 90% of the formulation, or mixtures of them. The formulation of saponins and chromans derivatives mixtures, mixed the formula shown in FIG. 1 related with synthetic chroman derivates compounds in a range from 10% until 80% of the formulation mixed with compounds of the formula shown in FIG. 2 related with extract of *Sapindus saponaria* resin mixed these with structures of the compound 1A, compound 2A and compound 3A in a range of the mixed extract from 20% until 90% of the formulation for parenteral use and/or topical use. The formula shown in FIG. 2 related with extract of *Sapindus saponaria* resin and mixed with structures of the compound 1A in range from 20% until 90% of the formulation, compound 2A in range from 20% until 90% of the formulation and compound 3A in range from 20% until 90% of the formulation, or mixtures of them.

The formula shown in FIG. 1 related with synthetic chroman derivates compounds are containing TC1, TC2, TC3, TC4, C18, wherein TC1, TC2, TC3, TC4, TC18 are showed in the following TABLE 1.

TABLE 1

Structure of TC1, TC2, TC3, TC4 and TC18

| PRODUCT | % YIELD | $^1$H |
|---|---|---|
| TC1 | 82% | $^1$H NMR (300 MHz, DMSO) δ 10.79 (s N – H), δ 7.87 (2-br 2H), δ 7.54 (m 4H), δ 7.24 (s-br 3H), δ 7.16 (d-br 1H), δ 3.07 (s br 4H) |

TABLE 1-continued

Structure of TC1, TC2, TC3, TC4 and TC18

| PRODUCT | % YIELD | $^1$H |
|---|---|---|
| TC2 | 78% | $^1$H NMR (300 MHz, DMSO) δ 10.47 (s N – H), δ 7.95 (d-br 3H), δ 7.36 (d 2H), δ 7.17 (d-br 2H), δ 7.09 (d-br 1H), δ 2.95 (t 2H), δ 2.84 (t 2H) |
| TC3 | 78% | $^1$H NMR (300 MHz, DMSO) δ 9.87 (s N – H), δ 8.11 (d-br 1H), δ 8.03 (d-br 3H), δ 7.8 (d-br 2H), δ 7.63 (m 3H), δ 3.25 (t 2H), δ 2.36 (t 2H) |
| TC4 | 80% | $^1$H NMR (300 MHz, DMSO) δ 10.07 (s N – H), δ 8.89 (d 2H), δ 8.52 (d 1H), δ 7.81 (d 2H), δ 7.66 (m 2H), δ 7.02 (m 2H), δ 5.84 (d 2H) |
| TC18 | 95% | $^1$H NMR (300 MHz, CDCL$_3$) δ 8.25 (d 1H), δ 7.98 (dd 1H), δ 7.81 (dt 1H), δ 7.54 (dt 1H), δ 3.6 (t 2H), δ 3.13 (t) |

Formulation of saponins and chromans derivatives mixtures against leishmaniasis, american trypanosomiasis, malaria, african trypanosomiasis and fasciolosis is a formulation mixtures of synthetic chroman compounds selected from the group consisting of TC1, TC2, TC3, TC4 or TC18 or mixtures of them with extract of *Sapindus saponaria* resin, wherein TC1 in range from 10% until 80% of the formulation, TC2 in range from 10% until 80% of the formulation, TC3 in range from 10% until 80% of the formulation, TC4 in range from 10% until 80% of the formulation, TC18 in range from 10% until 80% of the formulation and *Sapindus saponaria* resin containing saponins in proportions from 20% until 90% of the formulation, or mixtures of TC1, TC2, TC3, TC4, TC18 in range from 10% until 80% of the formulation.

Extracts or compounds from *Sapindus saponaria* resin are selected from the group consisting of 1A, 2A or 3A or mixtures of them, wherein 1A in range from 20% until 90% of the formulation, 2A in range from 20% until 90% of the formulation, 3A in range from 20% until 90% of the formulation or mixtures of 1A, 2A, 3A in range from 20% until 90% of the formulation. The saponins mixtures from the extract of *Sapindus saponaria* resin is selected from the group consisting of 1A, 2A or 3A, wherein 1A in range from 30% until 40% of the saponins mixtures, 2A in range from 30% until 40% of the saponins mixtures, 3A in range from 30% until 40% of the saponins mixtures.

Coupling Reaction

Figure 3:
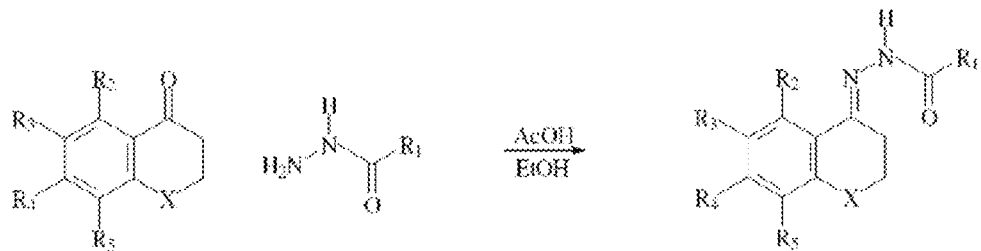
FIG. 3 shows the general reaction to obtain chroman derivative, according to the present invention.

FIG. 3 depicts the reaction to obtain chroman derivatives.

Benzoic acid, 2-(2,3-dihydro-4H-1-benzothiopyran-4-ylidene)hydrazide

A solution of thiochroman-4-one (0.493 g, 0.03 mol), benzoic hidrazide (0,491 g, 0.036 mol) in absolute ethanol (6.0 mL) and a catalytic amount of acetic acid (50 μl) in absolute ethanol (2.0 mL), was added dropwise. The reaction mixture was heated to reflux for 4 h and then poured into an ice/water, filtered, dried and crystallized from ethanol.

4-Pyridinecarboxylic acid, 2-(2,3-dihydro-4H-1-benzothiopyran-4-ylidene)hydrazid A solution of thiochroman-4-one (0.493 g, 0.03 mol), isoniazid (0,494 g, 0.036 mol) in absolute ethanol (6.0 mL) and a catalytic amount of acetic acid (50 µl) in absolute ethanol (2.0 mL), was added dropwise. The reaction mixture was heated to reflux for 4 h and then poured into an ice/water, filtered, dried and crystallized from ethanol.

Benzoic acid, 2-(2,3-dihydro-1,1-dioxido-4H-1-benzothiopyran-4-ylidene)hydrazide A solution of Thiochroman-4-one, 1,1-dioxide (0.589 g, 0.03 mol), benzoic hidrazide (0,491 g, 0.036 mol) in absolute ethanol (6.0 mL) and a catalytic amount of acetic acid (50 µl) in absolute ethanol (2.0 mL), was added dropwise. The reaction mixture was heated to reflux for 4 h and then poured into an ice/water, filtered, dried and crystallized from ethanol
Sulphone Obtention Thiochrom-4-one (200 mg, 1.22 mmol) was dissolved in acetic acid (800 µL, 1.40 mmol), and then $H_2O_2$ (800 µL, 7.80 mmol) was added dropwise. The mixture of reaction was stirred and maintained at room temperature during 2 hours; after, was poured into ice and extracted with $CH_2Cl_2$ (3×300 mL). Finally, organic layer was washed with $KHCO_3$, dried with MgSO4 and evaporated under vacuum; the compound was purified by column chromatography on silica gel, using n-hexane: AcOEt 80: 20 v/v)
Invention Analysis The formulation has been tested in vitro and in vivo for their leishmaninicidal activity. The compounds TC1, TC2, TC18, 1A, 2A and 3A exhibited activity against *Leishmania* parasites as shown in FIG. 4 and FIG. 5.

Figure 4:
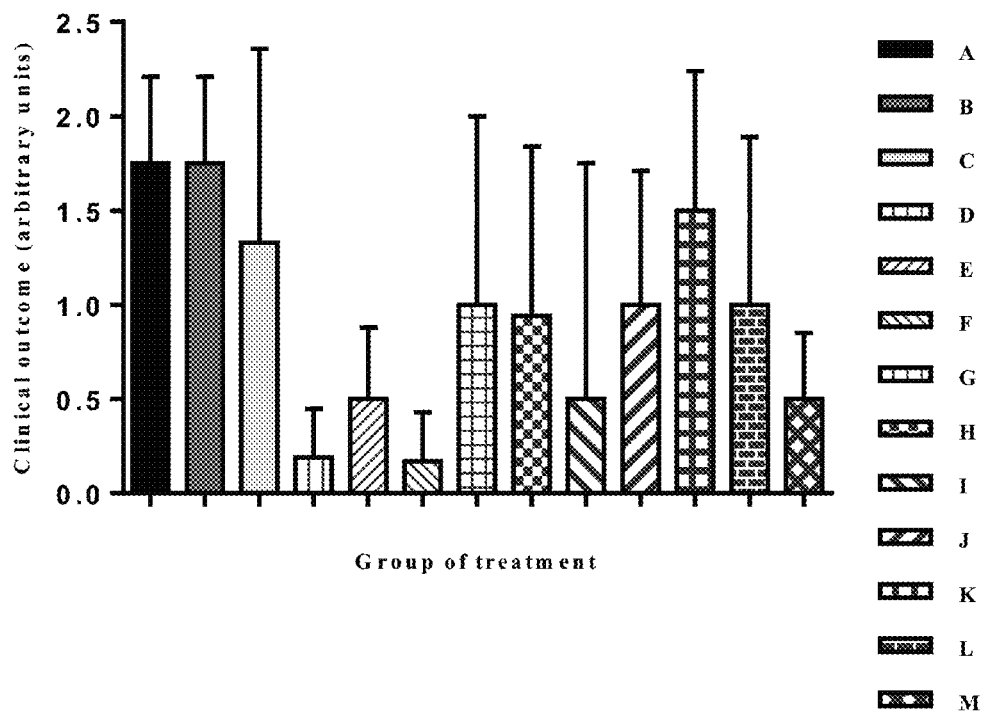
FIG. 4 illustrates in vivo therapeutic response of hamsters experimentally infected with *L. amazonensis* and treated with compounds, according to the present invention.

FIG. 4 shows the In vivo therapeutic response of hamsters experimentally infected with *L. amazonensis* and treated with compounds. FIG. 4 shows the clinical outcome at the end of the study (3 months after the end of treatment). The x-axis shows the group of treatment and the y-axis shows the arbitrary scale of measurement where 0 values is failure, 0.5 is relapse, 1 is clinical improvement and 2 is complete cure. A. TC1 (1.13 mg), B TC1 (4.01%), C: TC2 (1.35 mg), D: TC2 (3.0%), E: TC3 (1.72 mg), F: TC4 (1.25 mg), G: TC4 (4.03%), H: TC18 (3.0%), I: Mixture 1A, 2A, 3A (4.14%), J: Mixture 1A, 2A, 3A (7.77%), K: meglumina antimoniate (1209 mg), L: Vehicle (100 µl) and M: Vehicle (40 mg). The dot line shows the average value observed with the standard treatment (meglumina antimoniate). When comparing the sizes of the lesions during the study, at baseline was found that in animals treated with compound TC1 and compound TC2 showed the lowest lesion size since the second month after the end of the treatment to the end of the study.

Figure 5:
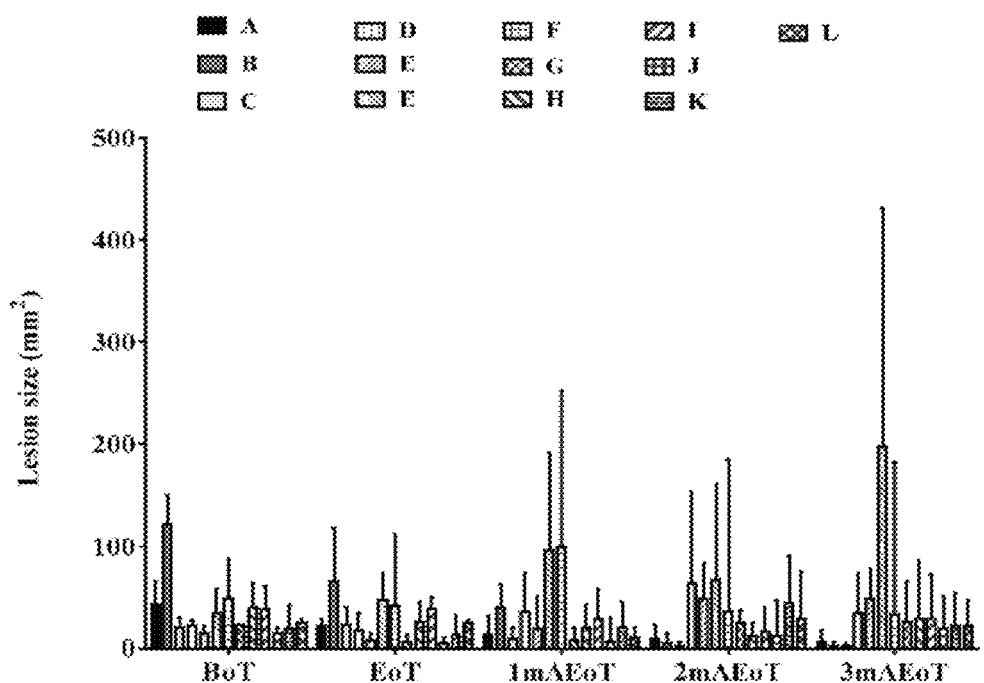
FIG. 5 illustrates another in vivo therapeutic response of hamsters experimentally infected with *L. amazonensis* and treated with compounds Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

FIG. 5 shows the In vivo therapeutic response of hamsters experimentally infected with *L. amazonensis* and treated with compounds. FIG. 5 shows the lesion size in mm2 according to each group of treatment. FIG. A. TC1 (1.13 mg), B TC1 (4.01%), C: TC2 (1.35 mg), D: TC2 (3.0%), E: TC3 (1.72 mg), F: TC4 (1.25 mg), G: TC4 (4.03%), H: TC18 (3.0%), I: Mixture 1A, 2A, 3A (4.14%), J: Mixture 1A, 2A, 3A (7.77%), K: meglumina antimoniate (1209 mg), L: Vehicle (100 µl) and M: Vehicle (40 mg). BoT: Beginning of Treatment; EoT: End of treatment. 1mAEoT: 1 month after the end of treatment, 2mAEoT: 2 months after the end of treatment, 3mAEoT: 3 months after the end of treatment. When these compounds were tested in the hamster model for cutaneous leishmaniasis, a cure rate of 77% was observed for the compound TC1 and 63% with compound TC18. Treatment with other compounds showed cure rates ranged from 30% to 50%. The efficacy may be increased using other dose or therapeutic schemes.

According to the following compound, the examples set out below illustrate the invention of the formulation synthetic chroman derivates mixed with extract of *Sapindus saponaria* resin:

TC1: $^1$H NMR (300 MHz, DMSO) δ 10.79 (s N—H), δδ 7.87 (2-br 2H), δ 7.54 (m 4H), δ 7.24 (s-br 3H), δ 7.16 (d-br 1H), δ 3.07 (s br 4H),

TC2: $^1$H NMR (300 MHz, DMSO) δ 10.47 (s N—H), δ 7.95 (d-br 3H), δ 7.36 (d 2H), δ 7.17 (d-br 2H), δ 7.09 (d-br 1H), δ 2.95 (t 2H), δ 2.84 (t 2H),

TC3: $^1$H NMR (300 MHz, DMSO) δ 9.87 (s N—H), δ 8.11 (d-br 1H), δ 8.03 (d-br 3H), δ 7.8 (d-br 2H), δ 7.63 (m 3H), δ 3.25 (t 2H), δ 2.36 (t 2H),

TC4: $^1$H NMR (300 MHz, DMSO) δ 10.07 (s N—H), δ 8.89 (d 2H), δ 8.52 (d 1H), δ 7.81 (d 2H), δ 7.66 (m 2H), δ 7.02 (m 2H), δ 5.84 (d 2H),

TC18:
$^1$H NMR (300 MHz, $CDCL_3$) δ 8.25 (d 1H), δ 7.98 (dd 1H), δ 7.81 (dt 1H), δ 7.54 (dt 1H), δ 3.6 (t 2H), δ 3.13 (t),

1A: $C_{48}H_{76}O_{17}$
2A: $C_{50}H_{78}O_{18}$
3A: $C_{50}H_{78}O_{18}$

Example 1

For the Formulation Synthetic Chroman Derivates Mixed with Extract of *Sapindus saponaria* Resin Formulation of synthetic chroman derivates compounds mixed with compounds of extract of *Sapindus saponaria* resin containing TC1 in 10% and saponins mixtures in 90% which in turn contains a mixture of 1A in 40%, 2A in 30% and 3A in 30%, or Formulation of synthetic chroman derivates compounds mixed with compounds of extract of *Sapindus saponaria* resin containing TC1 in 20% and saponins mixtures in 80% which in turn contains a mixture of 1A in 40%, 2A in 30% and 3A in 30%, or Formulation of synthetic chroman derivates compounds mixed with compounds of extract of *Sapindus saponaria* resin containing TC1 in 30% and saponins mixtures in 70% which in turn contains a mixture of 1A in 40%, 2A in 30% and 3A in 30%, or Formulation of synthetic chroman derivates compounds mixed with compounds of extract of *Sapindus saponaria* resin containing TC1 in 40% and saponins mixtures in 60% which in turn contains a mixture of 1A in 40%, 2A in 30% and 3A in 30%, or Formulation of synthetic chroman derivates compounds mixed with compounds of extract of *Sapindus saponaria* resin containing TC1 in 50% and saponins mixtures in 50% which in turn contains a mixture of 1A in 40%, 2A in 30% and 3A in 30%, or Formulation of synthetic chroman derivates compounds mixed with compounds of extract of *Sapindus saponaria* resin containing TC2 in 10% and saponins mixtures in 90% which in turn contains a mixture of 1A in 40%, 2A in 30% and 3A in 30%, or Formulation of synthetic chroman derivates compounds mixed with compounds of extract of *Sapindus saponaria* resin containing TC2 in 20% and saponins mixtures in 80% which in turn contains a mixture of 1A in 40%, 2A in 30% and 3A in 30%, or Formulation of synthetic chroman derivates compounds mixed with compounds of extract of *Sapindus saponaria* resin containing TC2 in 30% and saponins mixtures in 70% which in turn contains a mixture of 1A in 40%, 2A in 30% and 3A in 30%, or Formulation of synthetic chroman derivates compounds mixed with compounds of extract of *Sapindus saponaria* resin containing TC2 in 40% and saponins mixtures in 60% which in turn contains a mixture of 1A in 40%, 2A in 30% and 3A in 30%, or Formulation of synthetic chroman derivates compounds mixed with compounds of extract of *Sapindus saponaria* resin containing TC2 in 50% and saponins mixtures in 50% which in turn contains a mixture of 1A in 40%, 2A in 30% and 3A in 30%, or *Sapindus saponaria* resin containing TC3 in 10% and saponins mixtures in 90% which in turn contains a mixture of 1A in 40%, 2A in 30% and 3A in 30%, or Formulation of synthetic chroman derivates compounds mixed with compounds of extract of *Sapindus saponaria* resin containing TC3 in 20% and saponins mixtures in 80% which in turn contains a mixture of 1A in 40%, 2A in 30% and 3A in 30%, or Formulation of synthetic chroman derivates compounds mixed with compounds of extract of *Sapindus saponaria* resin containing TC3 in 30% and saponins mixtures in 70% which in turn contains a mixture of 1A in 40%, 2A in 30% and 3A in 30%, or Formulation of synthetic chroman derivates compounds mixed with compounds of extract of *Sapindus saponaria* resin containing TC3 in 40% and saponins mixtures in 60% which in turn contains a mixture of 1A in 40%, 2A in 30% and 3A in 30%, or Formulation of synthetic chroman derivates compounds mixed with compounds of extract of *Sapindus saponaria* resin containing TC3 in 50% and saponins mixtures in 50% which in turn contains a mixture of 1A in 40%, 2A in 30% and 3A in 30%, or *Sapindus saponaria* resin containing TC4 in 10% and saponins mixtures in 90% which in turn contains a mixture of 1A in 40%, 2A in 30% and 3A in 30%, or Formulation of synthetic chroman derivates compounds mixed with compounds of extract of *Sapindus saponaria* resin containing TC4 in 20% and saponins mixtures in 80% which in turn contains a mixture of 1A in 40%, 2A in 30% and 3A in 30%, or Formulation of synthetic chroman derivates compounds mixed with compounds of extract of *Sapindus saponaria* resin containing TC4 in 30% and saponins mixtures in 70% which in turn contains a mixture of 1A in 40%, 2A in 30% and 3A in 30%, or Formulation of synthetic chroman derivates compounds mixed with compounds of extract of *Sapindus saponaria* resin containing TC4 in 40% and saponins mixtures in 60% which in turn contains a mixture of 1A in 40%, 2A in 30% and 3A in 30%, or Formulation of synthetic chroman derivates compounds mixed with compounds of extract of *Sapindus saponaria* resin containing TC4 in 50% and saponins mixtures in 50% which in turn contains a mixture of 1A in 40%, 2A in 30% and 3A in 30%, or Formulation of synthetic chroman derivates compounds mixed with compounds of extract of *Sapindus saponaria* resin containing TC3 in 10% and saponin compound 1A in 90%.

Formulation of synthetic chroman derivates compounds mixed with compounds of extract of *Sapindus saponaria* resin containing TC3 in 20% and saponin compound 1A in 80%.

Formulation of synthetic chroman derivates compounds mixed with compounds of extract of *Sapindus saponaria* resin containing TC3 in 30% and saponin compound 1A in 70%.

Formulation of synthetic chroman derivates compounds mixed with compounds of extract of *Sapindus saponaria* resin containing TC3 in 40% and saponin compound 1A in 60%.

Formulation of synthetic chroman derivates compounds mixed with compounds of extract of *Sapindus saponaria* resin containing TC3 in 50% and saponin compound 1A in 50%.

Formulation of synthetic chroman derivates compounds mixed with compounds of extract of *Sapindus saponaria* resin containing TC4 in 10% and saponin compound 1A in 90%.

Formulation of synthetic chroman derivates compounds mixed with compounds of extract of *Sapindus saponaria* resin containing TC4 in 20% and saponin compound 1A in 80%.

Formulation of synthetic chroman derivates compounds mixed with compounds of extract of *Sapindus saponaria* resin containing TC4 in 30% and saponin compound 1A in 70%.

Formulation of synthetic chroman derivates compounds mixed with compounds of extract of *Sapindus saponaria* resin containing TC4 in 40% and saponin compound 1A in 60%.

Formulation of synthetic chroman derivates compounds mixed with compounds of extract of *Sapindus saponaria* resin containing TC4 in 50% and saponin compound 1A in 50%.

Formulation of synthetic chroman derivates compounds mixed with compounds of extract of *Sapindus saponaria* resin containing TC18 in 10% and saponins mixtures in 90% which in turn contains a mixture of 1A in 40%, 2A in 30% and 3A in 30%, or Formulation of synthetic chroman derivates compounds mixed with compounds of extract of *Sapindus saponaria* resin containing TC18 in 20% and saponins mixtures in 80% which in turn contains a mixture of 1A in 40%, 2A in 30% and 3A in 30%, or Formulation of synthetic chroman derivates compounds mixed with compounds of extract of *Sapindus saponaria* resin containing TC18 in 30% and saponins mixtures in 70% which in turn contains a mixture of 1A in 40%, 2A in 30% and 3A in 30%, or Formulation of synthetic chroman derivates compounds mixed with compounds of extract of *Sapindus saponaria* resin containing TC18 in 40% and saponins mixtures in 60% which in turn contains a mixture of 1A in 40%, 2A in 30% and 3A in 30%, or Formulation of synthetic chroman derivates compounds mixed with compounds of extract of *Sapindus saponaria* resin containing TC18 in 50% and saponins mixtures in 50% which in turn contains a mixture of 1A in 40%, 2A in 30% and 3A in 30%, or Example 2

For the Formulation Synthetic Chroman Derivates Mixed with Extract of *Sapindus saponaria* Resin Formulation of synthetic chroman derivates compounds mixed with compounds of extract of *Sapindus saponaria* resin containing TC1 in 10% and saponin compound 1A in 90%.

Formulation of synthetic chroman derivates compounds mixed with compounds of extract of *Sapindus saponaria* resin containing TC1 in 20% and saponin compound 1A in 80%.

Formulation of synthetic chroman derivates compounds mixed with compounds of extract of *Sapindus saponaria* resin containing TC1 in 30% and saponin compound 1A in 70%.

Formulation of synthetic chroman derivates compounds mixed with compounds of extract of *Sapindus saponaria* resin containing TC1 in 40% and saponin compound 1A in 60%.

Formulation of synthetic chroman derivates compounds mixed with compounds of extract of *Sapindus saponaria* resin containing TC1 in 50% and saponin compound 1A in 50%.

Formulation of synthetic chroman derivates compounds mixed with compounds of extract of *Sapindus saponaria* resin containing TC2 in 10% and saponin compound 1A in 90%.

Formulation of synthetic chroman derivates compounds mixed with compounds of extract of *Sapindus saponaria* resin containing TC2 in 20% and saponin compound 1A in 80%.

Formulation of synthetic chroman derivates compounds mixed with compounds of extract of *Sapindus saponaria* resin containing TC2 in 30% and saponin compound 1A in 70%.

Formulation of synthetic chroman derivates compounds mixed with compounds of extract of *Sapindus saponaria* resin containing TC2 in 40% and saponin compound 1A in 60%.

Formulation of synthetic chroman derivates compounds mixed with compounds of extract of *Sapindus saponaria* resin containing TC2 in 50% and saponin compound 1A in 50%.

Formulation of synthetic chroman derivates compounds mixed with compounds of extract of *Sapindus saponaria* resin containing TC3 in 10% and saponin compound 1A in 90%.

Formulation of synthetic chroman derivates compounds mixed with compounds of extract of *Sapindus saponaria* resin containing TC3 in 20% and saponin compound 1A in 80%.

Formulation of synthetic chroman derivates compounds mixed with compounds of extract of *Sapindus saponaria* resin containing TC3 in 30% and saponin compound 1A in 70%.

Formulation of synthetic chroman derivates compounds mixed with compounds of extract of *Sapindus saponaria* resin containing TC3 in 40% and saponin compound 1A in 60%.

Formulation of synthetic chroman derivates compounds mixed with compounds of extract of *Sapindus saponaria* resin containing TC3 in 50% and saponin compound 1A in 50%.

Formulation of synthetic chroman derivates compounds mixed with compounds of extract of *Sapindus saponaria* resin containing TC4 in 10% and saponin compound 1A in 90%.

Formulation of synthetic chroman derivates compounds mixed with compounds of extract of *Sapindus saponaria* resin containing TC4 in 20% and saponin compound 1A in 80%.

Formulation of synthetic chroman derivates compounds mixed with compounds of extract of *Sapindus saponaria* resin containing TC4 in 30% and saponin compound 1A in 70%.

Formulation of synthetic chroman derivates compounds mixed with compounds of extract of *Sapindus saponaria* resin containing TC4 in 40% and saponin compound 1A in 60%.

Formulation of synthetic chroman derivates compounds mixed with compounds of extract of *Sapindus saponaria* resin containing TC4 in 50% and saponin compound 1A in 50%.

Formulation of synthetic chroman derivates compounds mixed with compounds of extract of *Sapindus saponaria* resin containing TC18 in 10% and saponin compound 1A in 90%.

Formulation of synthetic chroman derivates compounds mixed with compounds of extract of *Sapindus saponaria* resin containing TC18 in 20% and saponin compound 1A in 80%.

Formulation of synthetic chroman derivates compounds mixed with compounds of extract of *Sapindus saponaria* resin containing TC18 in 30% and saponin compound 1A in 70%.

Formulation of synthetic chroman derivates compounds mixed with compounds of extract of *Sapindus saponaria* resin containing TC18 in 40% and saponin compound 1A in 60%.

Formulation of synthetic chroman derivates compounds mixed with compounds of extract of *Sapindus saponaria* resin containing TC18 in 50% and saponin compound 1A in 50%.

Example 3

For the Formulation Synthetic Chroman Derivates Mixed with Extract of *Sapindus saponaria* Resin Formulation of synthetic chroman derivates compounds mixed with compounds of extract of *Sapindus saponaria* resin containing TC1 in 10% and saponin compound 2A in 90%.

Formulation of synthetic chroman derivates compounds mixed with compounds of extract of *Sapindus saponaria* resin containing TC1 in 20% and saponin compound 2A in 80%.

Formulation of synthetic chroman derivates compounds mixed with compounds of extract of *Sapindus saponaria* resin containing TC1 in 30% and saponin compound 2A in 70%.

Formulation of synthetic chroman derivates compounds mixed with compounds of extract of *Sapindus saponaria* resin containing TC1 in 40% and saponin compound 2A in 60%.

Formulation of synthetic chroman derivates compounds mixed with compounds of extract of *Sapindus saponaria* resin containing TC1 in 50% and saponin compound 2A in 50%.

Formulation of synthetic chroman derivates compounds mixed with compounds of extract of *Sapindus saponaria* resin containing TC2 in 10% and saponin compound 2A in 90%.

Formulation of synthetic chroman derivates compounds mixed with compounds of extract of *Sapindus saponaria* resin containing TC2 in 20% and saponin compound 2A in 80%.

Formulation of synthetic chroman derivates compounds mixed with compounds of extract of *Sapindus saponaria* resin containing TC2 in 30% and saponin compound 2A in 70%.

Formulation of synthetic chroman derivates compounds mixed with compounds of extract of *Sapindus saponaria* resin containing TC2 in 40% and saponin compound 2A in 60%.

Formulation of synthetic chroman derivates compounds mixed with compounds of extract of *Sapindus saponaria* resin containing TC2 in 50% and saponin compound 2A in 50%.

Formulation of synthetic chroman derivates compounds mixed with compounds of extract of

*Sapindus saponaria* resin containing TC3 in 10% and saponin compound 2A in 90%.

Formulation of synthetic chroman derivates compounds mixed with compounds of extract of *Sapindus saponaria* resin containing TC3 in 20% and saponin compound 2A in 80%.

Formulation of synthetic chroman derivates compounds mixed with compounds of extract of *Sapindus saponaria* resin containing TC3 in 30% and saponin compound 2A in 70%.

Formulation of synthetic chroman derivates compounds mixed with compounds of extract of *Sapindus saponaria* resin containing TC3 in 40% and saponin compound 2A in 60%.

Formulation of synthetic chroman derivates compounds mixed with compounds of extract of *Sapindus saponaria* resin containing TC3 in 50% and saponin compound 2A in 50%.

*Sapindus saponaria* resin containing TC4 in 10% and saponin compound 2A in 90%.

Formulation of synthetic chroman derivates compounds mixed with compounds of extract of *Sapindus saponaria* resin containing TC4 in 20% and saponin compound 2A in 80%.

Formulation of synthetic chroman derivates compounds mixed with compounds of extract of *Sapindus saponaria* resin containing TC4 in 30% and saponin compound 2A in 70%.

Formulation of synthetic chroman derivates compounds mixed with compounds of extract of *Sapindus saponaria* resin containing TC4 in 40% and saponin compound 2A in 60%.

Formulation of synthetic chroman derivates compounds mixed with compounds of extract of *Sapindus saponaria* resin containing TC4 in 50% and saponin compound 2A in 50%.

Formulation of synthetic chroman derivates compounds mixed with compounds of extract of *Sapindus saponaria* resin containing TC18 in 10% and saponin compound 2A in 90%.

Formulation of synthetic chroman derivates compounds mixed with compounds of extract of *Sapindus saponaria* resin containing TC18 in 20% and saponin compound 2A in 80%.

Formulation of synthetic chroman derivates compounds mixed with compounds of extract of *Sapindus saponaria* resin containing TC18 in 30% and saponin compound 2A in 70%.

Formulation of synthetic chroman derivates compounds mixed with compounds of extract of *Sapindus saponaria* resin containing TC18 in 40% and saponin compound 2A in 60%.

Formulation of synthetic chroman derivates compounds mixed with compounds of extract of *Sapindus saponaria* resin containing TC18 in 50% and saponin compound 2A in 50%.

Example 4

For the Formulation Synthetic Chroman Derivates Mixed with Extract of *Sapindus saponaria* Resin Formulation of synthetic chroman derivates compounds mixed with compounds of extract of *Sapindus saponaria* resin containing TC1 in 10% and saponin compound 3A in 90%.

Formulation of synthetic chroman derivates compounds mixed with compounds of extract of *Sapindus saponaria* resin containing TC1 in 20% and saponin compound 3A in 80%.

Formulation of synthetic chroman derivates compounds mixed with compounds of extract of *Sapindus saponaria* resin containing TC1 in 30% and saponin compound 3A in 70%.

Formulation of synthetic chroman derivates compounds mixed with compounds of extract of *Sapindus saponaria* resin containing TC1 in 40% and saponin compound 3A in 60%.

Formulation of synthetic chroman derivates compounds mixed with compounds of extract of *Sapindus saponaria* resin containing TC1 in 50% and saponin compound 3A in 50%.

Formulation of synthetic chroman derivates compounds mixed with compounds of extract of *Sapindus saponaria* resin containing TC2 in 10% and saponin compound 3A in 90%.

Formulation of synthetic chroman derivates compounds mixed with compounds of extract of *Sapindus saponaria* resin containing TC2 in 20% and saponin compound 3A in 80%.

Formulation of synthetic chroman derivates compounds mixed with compounds of extract of *Sapindus saponaria* resin containing TC2 in 30% and saponin compound 3A in 70%.

Formulation of synthetic chroman derivates compounds mixed with compounds of extract of *Sapindus saponaria* resin containing TC2 in 40% and saponin compound 3A in 60%.

Formulation of synthetic chroman derivates compounds mixed with compounds of extract of *Sapindus saponaria* resin containing TC2 in 50% and saponin compound 3A in 50%.

Formulation of synthetic chroman derivates compounds mixed with compounds of extract of *Sapindus saponaria* resin containing TC3 in 10% and saponin compound 3A in 90%.

Formulation of synthetic chroman derivates compounds mixed with compounds of extract of *Sapindus saponaria* resin containing TC3 in 20% and saponin compound 3A in 80%.

Formulation of synthetic chroman derivates compounds mixed with compounds of extract of *Sapindus saponaria* resin containing TC3 in 30% and saponin compound 3A in 70%.

Formulation of synthetic chroman derivates compounds mixed with compounds of extract of *Sapindus saponaria* resin containing TC3 in 40% and saponin compound 3A in 60%.

Formulation of synthetic chroman derivates compounds mixed with compounds of extract of *Sapindus saponaria* resin containing TC3 in 50% and saponin compound 3A in 50%.

Formulation of synthetic chroman derivates compounds mixed with compounds of extract of *Sapindus saponaria* resin containing TC4 in 10% and saponin compound 3A in 90%.

Formulation of synthetic chroman derivates compounds mixed with compounds of extract of *Sapindus saponaria* resin containing TC4 in 20% and saponin compound 3A in 80%.

Formulation of synthetic chroman derivates compounds mixed with compounds of extract of *Sapindus saponaria* resin containing TC4 in 30% and saponin compound 3A in 70%.

Formulation of synthetic chroman derivates compounds mixed with compounds of extract of *Sapindus saponaria* resin containing TC4 in 40% and saponin compound 3A in 60%.

Formulation of synthetic chroman derivates compounds mixed with compounds of extract of *Sapindus saponaria* resin containing TC4 in 50% and saponin compound 3A in 50%.

Formulation of synthetic chroman derivates compounds mixed with compounds of extract of *Sapindus saponaria* resin containing TC18 in 10% and saponin compound 3A in 90%.

Formulation of synthetic chroman derivates compounds mixed with compounds of extract of *Sapindus saponaria* resin containing TC18 in 20% and saponin compound 3A in 80%.

Formulation of synthetic chroman derivates compounds mixed with compounds of extract of *Sapindus saponaria* resin containing TC18 in 30% and saponin compound 3A in 70%.

Formulation of synthetic chroman derivates compounds mixed with compounds of extract of *Sapindus saponaria* resin containing TC18 in 40% and saponin compound 3A in 60%.

Formulation of synthetic chroman derivates compounds mixed with compounds of extract of *Sapindus saponaria* resin containing TC18 in 50% and saponin compound 3A in 50%.

Example 5

For the Formulation Synthetic Chroman Derivates Mixed with Extract of *Sapindus saponaria* Resin Formulation of synthetic chroman derivates compounds mixed with compounds of extract of *Sapindus saponaria* resin containing TC1 in 10% and saponins mixtures in 90% which in turn contains a mixture of 1A in 30%, 2A in 40% and 3A in 30%, or Formulation of synthetic chroman derivates compounds mixed with compounds of extract of *Sapindus saponaria* resin containing TC1 in 20% and saponins mixtures in 80% which in turn contains a mixture of 1A in 30%, 2A in 40% and 3A in 30%, or Formulation of synthetic chroman derivates compounds mixed with compounds of extract of *Sapindus saponaria* resin containing TC1 in 30% and saponins mixtures in 70% which in turn contains a mixture of 1A in 30%, 2A in 40% and 3A in 30%, or Formulation of synthetic chroman derivates compounds mixed with compounds of extract of *Sapindus saponaria* resin containing TC1 in 40% and saponins mixtures in 60% which in turn contains a mixture of 1A in 30%, 2A in 40% and 3A in 30%, or Formulation of synthetic chroman derivates compounds mixed with compounds of extract of *Sapindus saponaria* resin containing TC1 in 50% and saponins mixtures in 50% which in turn contains a mixture of 1A in 30%, 2A in 40% and 3A in 30%, or Formulation of synthetic chroman derivates compounds mixed with compounds of extract of *Sapindus saponaria* resin containing TC2 in 10% and saponins mixtures in 90% which in turn contains a mixture of 1A in 30%, 2A in 40% and 3A in 30%, or Formulation of synthetic chroman derivates compounds mixed with compounds of extract of *Sapindus saponaria* resin containing TC2 in 20% and saponins mixtures in 80% which in turn contains a mixture of 1A in 30%, 2A in 40% and 3A in 30%, or Formulation of synthetic chroman derivates compounds mixed with compounds of extract of *Sapindus saponaria* resin containing TC2 in 30% and saponins mixtures in 70% which in turn contains a mixture of 1A in 30%, 2A in 40% and 3A in 30%, or Formulation of synthetic chroman derivates compounds mixed with compounds of extract of *Sapindus saponaria* resin containing TC2 in 40% and saponins mixtures in 60% which in turn contains a mixture of 1A in 30%, 2A in 40% and 3A in 30%, or Formulation of synthetic chroman derivates compounds mixed with compounds of extract of *Sapindus saponaria* resin containing TC2 in 50% and saponins mixtures in 50% which in turn contains a mixture of 1A in 30%, 2A in 40% and 3A in 30%, or Formulation of synthetic chroman derivates compounds mixed with compounds of extract of *Sapindus saponaria* resin containing TC3 in 10% and saponins mixtures in 90% which in turn contains a mixture of 1A in 30%, 2A in 40% and 3A in 30%, or Formulation of synthetic chroman derivates compounds mixed with compounds of extract of *Sapindus saponaria* resin containing TC3 in 20% and saponins mixtures in 80% which in turn contains a mixture of 1A in 30%, 2A in 40% and 3A in 30%, or Formulation of synthetic chroman derivates compounds mixed with compounds of extract of *Sapindus saponaria* resin containing TC3 in 30% and saponins mixtures in 70% which in turn contains a mixture of 1A in 30%, 2A in 40% and 3A in 30%, or Formulation of synthetic chroman derivates compounds mixed with compounds of extract of *Sapindus saponaria* resin containing TC3 in 40% and saponins mixtures in 60% which in turn contains a mixture of 1A in 30%, 2A in 40% and 3A in 30%, or Formulation of synthetic chroman derivates compounds mixed with compounds of extract of *Sapindus saponaria* resin containing TC3 in 50% and saponins mixtures in 50% which in turn contains a mixture of 1A in 30%, 2A in 40% and 3A in 30%, or Formulation of synthetic chroman derivates compounds mixed with compounds of extract of *Sapindus saponaria* resin containing TC4 in 10% and saponins mixtures in 90% which in turn contains a mixture of 1A in 30%, 2A in 40% and 3A in 30%, or Formulation of synthetic chroman derivates compounds mixed with compounds of extract of *Sapindus saponaria* resin containing TC4 in 20% and saponins mixtures in 80% which in turn contains a mixture of 1A in 30%, 2A in 40% and 3A in 30%, or Formulation of synthetic chroman derivates compounds mixed with compounds of extract of *Sapindus saponaria* resin containing TC4 in 30% and saponins mixtures in 70% which in turn contains a mixture of 1A in 30%, 2A in 40% and 3A in 30%, or Formulation of synthetic chroman derivates compounds mixed with compounds of extract of *Sapindus saponaria* resin containing TC4 in 40% and saponins mixtures in 60% which in turn contains a mixture of 1A in 30%, 2A in 40% and 3A in 30%, or Formulation of synthetic chroman derivates compounds mixed with compounds of extract of *Sapindus saponaria* resin containing TC4 in 50% and saponins mixtures in 50% which in turn contains a mixture of 1A in 30%, 2A in 40% and 3A in 30%, or Formulation of synthetic chroman derivates compounds mixed with compounds of extract of *Sapindus saponaria* resin containing TC18 in 10% and saponins mixtures in 90% which in turn contains a mixture of 1A in 30%, 2A in 40% and 3A in 30%, or Formulation of synthetic chroman derivates compounds mixed with compounds of extract of *Sapindus saponaria* resin containing TC18 in 20% and saponins mixtures in 80% which in turn contains a mixture of 1A in 30%, 2A in 40% and 3A in 30%, or Formulation of synthetic chroman derivates compounds mixed with compounds of extract of *Sapindus saponaria* resin containing TC18 in 30% and saponins mixtures in 70% which in turn contains a mixture of 1A in 30%, 2A in 40% and 3A in 30%, or Formulation of synthetic chroman derivates compounds mixed with compounds of extract of *Sapindus saponaria* resin containing TC18 in 40% and saponins mixtures in 60% which in turn contains a mixture of 1A in 30%, 2A in 40% and 3A in 30%, or Formulation of synthetic chroman derivates compounds mixed with compounds of extract of *Sapindus saponaria* resin containing TC18 in 50% and saponins mixtures in 50% which in turn contains a mixture of 1A in 30%, 2A in 40% and 3A in 30%.

Example 6

For the Formulation Synthetic Chroman Derivates Mixed with Extract of *Sapindus saponaria* Resin Formulation of synthetic chroman derivates compounds mixed with compounds of extract of *Sapindus saponaria* resin containing TC1 in 10% and saponins mixtures in 90% which in turn contains a mixture of 1A in 30%, 2A in 30% and 3A in 40%, or Formulation of synthetic chroman derivates compounds mixed with compounds of extract of *Sapindus saponaria* resin containing TC1 in 20% and saponins mixtures in 80% which in turn contains a mixture of 1A in 30%, 2A in 30% and 3A in 40%, or Formulation of synthetic chroman derivates compounds mixed with compounds of extract of *Sapindus saponaria* resin containing TC1 in 30% and saponins mixtures in 70% which in turn contains a mixture of 1A in 30%, 2A in 30% and 3A in 40%, or Formulation of synthetic chroman derivates compounds mixed with compounds of extract of *Sapindus saponaria* resin containing TC1 in 40% and saponins mixtures in 60% which in turn contains a mixture of 1A in 30%, 2A in 30% and 3A in 40%, or Formulation of synthetic chroman derivates compounds mixed with compounds of extract of *Sapindus saponaria* resin containing TC1 in 50% and saponins mixtures in 50% which in turn contains a mixture of 1A in 30%, 2A in 30% and 3A in 40%, or Formulation of synthetic chroman derivates compounds mixed with compounds of extract of *Sapindus saponaria* resin containing TC2 in 10% and saponins mixtures in 90% which in turn contains a mixture of 1A in 30%, 2A in 30% and 3A in 40%, or Formulation of synthetic chroman derivates compounds mixed with compounds of extract of *Sapindus saponaria* resin containing TC2 in 20% and saponins mixtures in 80% which in turn contains a mixture of 1A in 30%, 2A in 30% and 3A in 40%, or Formulation of synthetic chroman derivates compounds mixed with compounds of extract of *Sapindus saponaria* resin containing TC2 in 30% and saponins mixtures in 70% which in turn contains a mixture of 1A in 30%, 2A in 30% and 3A in 40%, or Formulation of synthetic chroman derivates compounds mixed with compounds of extract of *Sapindus saponaria* resin containing TC2 in 40% and saponins mixtures in 60% which in turn contains a mixture of 1A in 30%, 2A in 30% and 3A in 40%, or Formulation of synthetic chroman derivates compounds mixed with compounds of extract of *Sapindus saponaria* resin containing TC2 in 50% and saponins mixtures in 50% which in turn contains a mixture of 1A in 30%, 2A in 30% and 3A in 40%, or Formulation of synthetic chroman derivates compounds mixed with compounds of extract of *Sapindus saponaria* resin containing TC3 in 10% and saponins mixtures in 90% which in turn contains a mixture of 1A in 30%, 2A in 30% and 3A in 40%, or Formulation of synthetic chroman derivates compounds mixed with compounds of extract of *Sapindus saponaria* resin containing TC3 in 20% and saponins mixtures in 80% which in turn contains a mixture of 1A in 30%, 2A in 30% and 3A in 40%, or Formulation of synthetic chroman derivates compounds mixed with compounds of extract of *Sapindus saponaria* resin containing TC3 in 30% and saponins mixtures in 70% which in turn contains a mixture of 1A in 30%, 2A in 30% and 3A in 40%, or Formulation of synthetic chroman derivates compounds mixed with compounds of extract of *Sapindus saponaria* resin containing TC3 in 40% and saponins mixtures in 60% which in turn contains a mixture of 1A in 30%, 2A in 30% and 3A in 40%, or Formulation of synthetic chroman derivates compounds mixed with compounds of extract of *Sapindus saponaria* resin containing TC3 in 50% and saponins mixtures in 50% which in turn contains a mixture of 1A in 30%, 2A in 30% and 3A in 40%. *Sapindus saponaria* resin containing TC4 in 10% and saponins mixtures in 90% which in turn contains a mixture of 1A in 30%, 2A in 30% and 3A in 40%, or Formulation of synthetic chroman derivates compounds mixed with compounds of extract of *Sapindus saponaria* resin containing TC4 in 20% and saponins mixtures in 80% which in turn contains a mixture of 1A in 30%, 2A in 30% and 3A in 40%, or Formulation of synthetic chroman derivates compounds mixed with compounds of extract of *Sapindus saponaria* resin containing TC4 in 30% and saponins mixtures in 70% which in turn contains a mixture of 1A in 30%, 2A in 30% and 3A in 40%, or Formulation of synthetic chroman derivates compounds mixed with compounds of extract of *Sapindus saponaria* resin containing TC4 in 40% and saponins mixtures in 60% which in turn contains a mixture of 1A in 30%, 2A in 30% and 3A in 40%, or Formulation of synthetic chroman derivates compounds mixed with compounds of extract of *Sapindus saponaria* resin containing TC4 in 50% and saponins mixtures in 50% which in turn contains a mixture of 1A in 30%, 2A in 30% and 3A in 40%. Formulation of synthetic chroman derivates compounds mixed with compounds of extract of *Sapindus saponaria* resin containing TC18 in 10% and saponins mixtures in 90% which in turn contains a mixture of 1A in 30%, 2A in 30% and 3A in 40%, or Formulation of synthetic chroman derivates compounds mixed with compounds of extract of *Sapindus saponaria* resin containing TC18 in 20% and saponins mixtures in 80% which in turn contains a mixture of 1A in 30%, 2A in 30% and 3A in 40%, or Formulation of synthetic chroman derivates compounds mixed with compounds of extract of *Sapindus saponaria* resin containing TC18 in 30% and saponins mixtures in 70% which in turn contains a mixture of 1A in 30%, 2A in 30% and 3A in 40%, or Formulation of synthetic chroman derivates compounds mixed with compounds of extract of *Sapindus saponaria* resin containing TC18 in 40% and saponins mixtures in 60% which in turn contains a mixture of 1A in 30%, 2A in 30% and 3A in 40%, or Formulation of synthetic chroman derivates compounds mixed with compounds of extract of *Sapindus saponaria* resin containing TC18 in 50% and saponins mixtures in 50% which in turn contains a mixture of 1A in 30%, 2A in 30% and 3A in 40%.

Because many varying and differing embodiments maybe made within the scope of the inventive concept herein taught and because many modifications may be made in the embodiment herein detailed in accordance with the descriptive requirement of the law, it is to be understood that the details herein are to be interpreted as illustrative and not in a limiting sense.

We claim:

1. A composition comprising: chroman derivatives of formula 1,

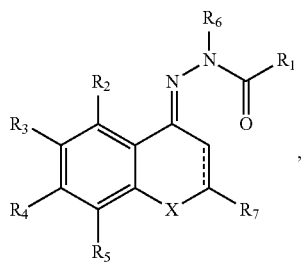

in a range of 10%-80% by weight of the composition and saponins of formula 2:

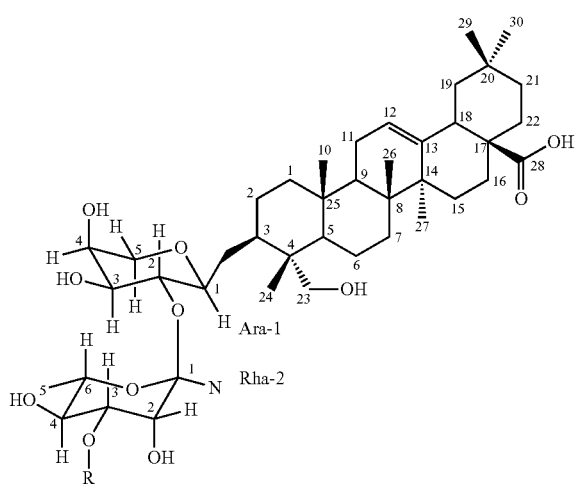

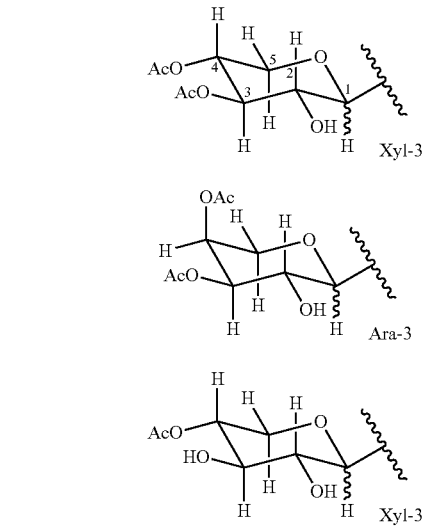

having R selected from the group consisting of: 1A, 1B and 1C, in a range of 20%-90% by weight of the composition wherein:

X represents O, NH, S, S=O, S(O)$_2$, or CH$_2$ and may or may not have a double bond in the position indicated by the figure as a dashed line, R$_1$ represent phenyl, naphthyl, aromatic or non aromatic 5-6 membered hetero ring containing at least one of: 1-2 N atoms, 0-1 O atoms and 0-1 S atoms, mono or di substituted with substituent selected from the group consisting of: OH, CHO, OCH$_3$, NO$_2$, NH$_2$, NHCOCH$_3$, COOH, COOCH$_3$, CH$_2$OH, CN, halogen, C$_1$-C$_6$ alkyl, C$_1$-C$_6$ alkylthio, C$_1$-C$_6$ haloalkyl, C$_1$-C$_6$ haloalkoxy or C$_1$-C$_6$ halothioalkyl, R$_2$, R$_3$, R$_4$, R$_5$, R$_6$ and R$_7$ independently represent H, OH, CHO, OCH$_3$, NO$_2$, NH$_2$, NHCOCH$_3$, COOH, COOCH$_3$, CH$_2$OH, CN, halogen, C$_1$-C$_6$ alkyl, C$_1$-C$_6$ alkylthio, C$_1$-C$_6$ haloalkyl, C$_1$-C$_6$ haloalkoxy or C$_1$-C$_6$ halothioalkyl, —O—S(=O)—R$_8$, N(R$_9$) SO$_2$R$_{10}$, benzyl, phenyl, R$_8$=C$_1$-C$_6$ alkyl, C$_1$-C$_6$ alkylthio, C$_1$-C$_6$ haloalkyl, C$_1$-C$_6$ haloalkoxy or C$_1$-C$_6$ halothioalkyl, and R$_9$ and R$_{10}$ are C$_1$-C$_6$ alkyl, C$_1$-C$_6$ haloalkyl, C$_1$-C$_6$ haloalkoxy or C$_1$-C$_6$ halothioalkyl, un substituted or mono or di substituted phenyl or pyridyl, with substituent selected from the group consisting of: H, OH, CHO, OCH$_3$, NO$_2$, NH$_2$, NHCOCH$_3$, COOH, COOCH$_3$, CH$_2$OH, CN, halogen, C$_1$-C$_6$ alkyl, C$_1$-C$_6$ alkylthio, C$_1$-C$_6$ haloalkyl, C$_1$-C$_6$ haloalkoxy or C$_1$-C$_6$ halothioalkyl, wherein the compounds are individual isomers, mixtures of isomers, tautomeric mixtures including syn or anti, cis or trans or R or S forms.

2. The composition according to claim 1, wherein the chroman derivatives of said formula 1 is selected from the group consisting of:

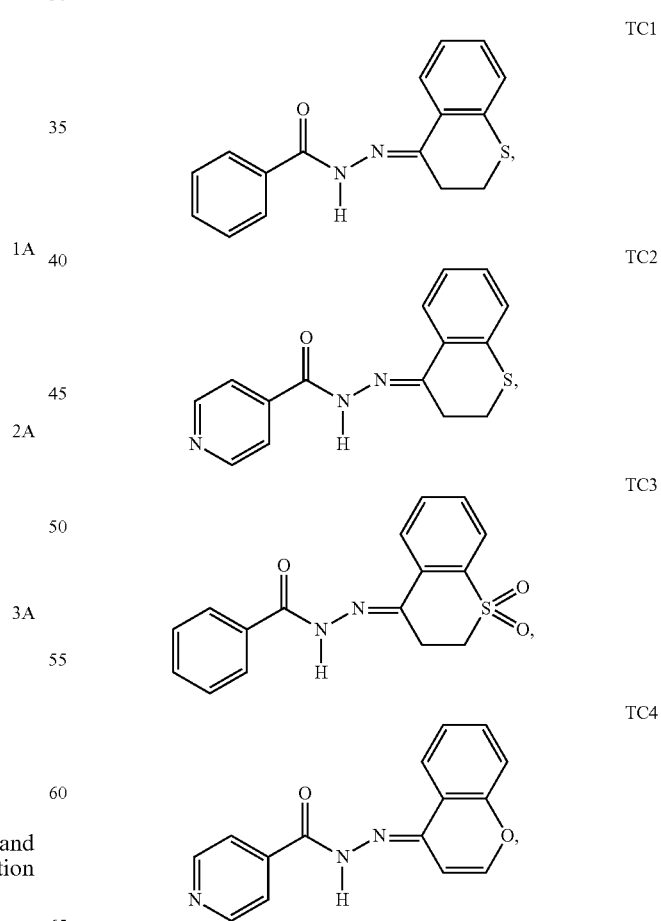

or mixtures thereof.

3. The composition according to claim 1, wherein R in the saponins of said formula 2 is selected from the group consisting of:

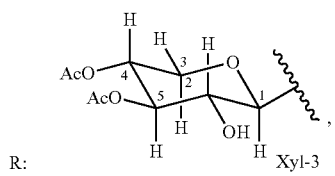
R: (1A)

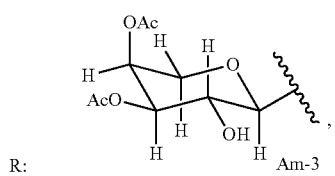
R: (2A)

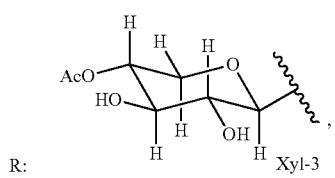
R: (3A)

or mixtures thereof.

4. The composition according to claim 3, wherein the composition comprises the saponin with formula 1A as R being 30-40% by weight of the saponins, the saponin with formula 1B as R being 30-40% by weight of the saponins and the saponin with formula 1C as R being 30-40% by weight of the saponins.

5. The composition according to claim 1, wherein the chroman derivatives of formula 1 are in a proportion of 80% by weight of the composition and the saponins of the formula 2 are in a proportion of 20% by weight of the composition.

6. The composition according to claim 1, wherein the composition comprises:

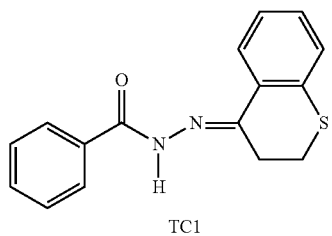
TC1 in 10-80% by weight of the composition and saponins in 20-90% by weight of the composition.

7. The composition according to claim 1, wherein the mixture comprises:

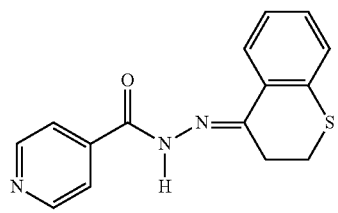
TC2 in 10-80% by weight of the composition and saponins in 20-90% by weight of the composition.

8. The composition according to claim 1, wherein the mixture comprises:

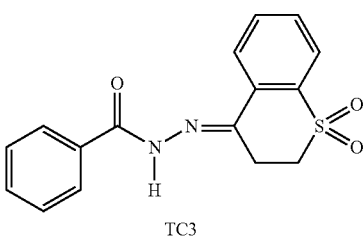
TC3 in 10-80% by weight of the composition and saponins in 20-90% by weight of the composition.

9. The composition according to claim 1, wherein the mixture comprises:

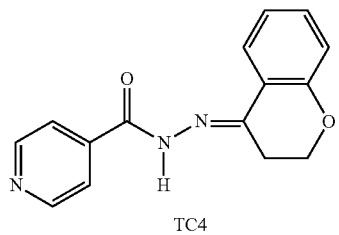
TC4 in 10-80% by weight of the composition and saponins in 20-90% by weight of the composition.

10. The composition according to claim 3, wherein the composition comprises the chroman derivatives of formula 1 in 10-80% by weight of the composition with saponins of formula 2 wherein R is the formula 1A in 20-90% by weight of the composition.

11. The composition according to claim 3, wherein the composition comprises the chroman derivatives of formula 1 in 10-80% of the composition with saponins of formula 2 wherein R is the formula 2A in 20-90% by weight of the composition.

12. The composition according to claim 3, wherein the composition comprises the chroman derivatives of formula 1 in 10-80% of the composition with saponins of formula 2 wherein R is the formula 3A in 20-90% by weight of the composition.

* * * * *